(12) United States Patent
Christiansen et al.

(10) Patent No.: US 10,709,853 B2
(45) Date of Patent: Jul. 14, 2020

(54) DEVICE

(71) Applicant: Intracair IVS, Odder (DK)

(72) Inventors: Karen Juelsgaard Christiansen, Aarhus C. (DK); Krister Just Kristensen, Hellerup (DK); Henrik Neuschäfer Larsen, Hellerup (DK)

(73) Assignee: Intracair IVS, Odder (DK)

( * ) Notice: Subject to any disclaimer, the term of this patent is extended or adjusted under 35 U.S.C. 154(b) by 749 days.

(21) Appl. No.: 15/322,510

(22) PCT Filed: Jun. 30, 2015

(86) PCT No.: PCT/EP2015/064892
§ 371 (c)(1),
(2) Date: Dec. 28, 2016

(87) PCT Pub. No.: WO2016/001251
PCT Pub. Date: Jan. 7, 2016

(65) Prior Publication Data
US 2017/0136197 A1    May 18, 2017

(30) Foreign Application Priority Data
Jun. 30, 2014    (GB) .................. 1411628.9

(51) Int. Cl.
*A61M 16/00* (2006.01)
*A61M 16/04* (2006.01)
*B29C 45/14* (2006.01)
*B29L 31/00* (2006.01)

(52) U.S. Cl.
CPC ........ *A61M 16/0003* (2014.02); *A61M 16/04* (2013.01); *A61M 16/0465* (2013.01); *A61M 2205/0266* (2013.01); *A61M 2205/32* (2013.01); *A61M 2207/00* (2013.01); *B29C 45/14786* (2013.01); *B29L 2031/7546* (2013.01)

(58) Field of Classification Search
CPC .......... A61M 16/0003; A61M 16/0465; A61M 2207/00; A61M 2205/32; A61M 16/04; A61M 2205/0266; A61M 16/0468; A61M 16/0472; A61M 16/047; B29L 2031/7546
See application file for complete search history.

(56) References Cited

U.S. PATENT DOCUMENTS 3,499,450 A * 3/1970 Rathjen ............. A61M 16/0465
128/207.17
5,287,852 A * 2/1994 Arkinstall ......... A61M 16/0465
128/200.24

(Continued)

FOREIGN PATENT DOCUMENTS

DE       4015186 A1    11/1991
DE    202005003601 U1     5/2005

*Primary Examiner* — Tu A Vo
(74) *Attorney, Agent, or Firm* — McCarter & English, LLP; Steven G. Davis; Wei Song

(57) ABSTRACT

A device for sealing a tracheostoma in a patient includes a seal member for insertion through the tracheostoma to a trachea. The seal member includes a disc having a predetermined line of weakness. In a first configuration, the seal member forms a seal by being pulled against the tracheostoma. In a second configuration, the seal member is removed from the trachea through the tracheostoma by breaking along the line of weakness.

20 Claims, 13 Drawing Sheets

(56) References Cited

U.S. PATENT DOCUMENTS

| | | | | |
|---|---|---|---|---|
| 6,612,305 B2* | 9/2003 | Fauza | ............... | A61M 16/0465 |
| | | | | 128/200.26 |
| 6,840,242 B1* | 1/2005 | McCoy | ............. | A61M 16/0465 |
| | | | | 128/207.14 |
| 6,971,382 B1* | 12/2005 | Corso | ..................... | A61F 2/203 |
| | | | | 128/200.26 |
| 2006/0260617 A1* | 11/2006 | Abolfathi | .......... | A61M 16/0465 |
| | | | | 128/207.29 |
| 2008/0275402 A1* | 11/2008 | Schnell | .............. | A61B 17/0057 |
| | | | | 604/175 |
| 2012/0145147 A1 | 6/2012 | Freitag et al. | | |

* cited by examiner

DEVICE

CROSS REFERENCE TO RELATED APPLICATIONS

This application is a U.S. national stage filing under 35 U.S.C. § 371(c), of International Application No. PCT/EP2015/064892, filed on Jun. 30, 2015, which claims foreign priority of U.K. Patent Application No. 1411628.9, filed on Jun. 30, 2014.

FIELD OF THE INVENTION

The present invention relates to a device for sealing a tracheostoma in a patient.

BACKGROUND OF THE INVENTION

A tracheostomy tube is a short curved tube inserted through a surgical hole in a patient's neck and held in place with a tracheostomy tie around the patient's neck. The purpose of a tracheostomy tube is to provide the patient with an airway or to provide the patient with an access that facilitates the suction of secretions from the airway.

Patients have tracheostomy tubes placed for numerous reasons. Once the reason that necessitated the placement of a tracheostomy tube has been resolved, the tracheostomy tube is normally removed. This procedure is known as decannulation. After the patient is decannulated, there remains a hole in the patient's neck which is known as a stoma. Once the patient is decannulated the stoma will usually close on its own in the majority of the patients. This normally occurs in two to three weeks. Surgical closure of the stoma is required for the patients whose stomas do not close on their own.

Currently, when a patient is decannulated, an occlusive or simply a gauze bandage type of arrangement is placed on the patient for days following decannulation. Once the patient leaves the hospital and in some cases even within the hospital such as from an Intensive Care Unit to a Regular Care Unit, the usual method of covering the stoma is to use the bandage. The patient is then instructed to cover the stoma with a finger when the patient needs to speak or cough.

This method of covering the stoma with the bandage, and using a finger to occlude the stoma in order to talk, suffers from a number of disadvantages. First, if the patient is a child, or a developmentally or physically disabled adult, he or she may not be able to occlude the stoma with a finger as needed. Second, in all patients, if the stoma is not covered in a somewhat airtight fashion, air passing in and out of the stoma when the patient attempts to talk, causes difficulty with or even makes it impossible for the patient to have the ability to speak. Third, when the patient coughs without covering the stoma, air is forced out of the stoma, and even normal breathing can cause air to pass in and out of the stoma if only covered by the bandage. This air movement through the stoma reduces the chance of the stoma closing on its own without surgery. Fourth, touching the stoma with the patient's fingers to talk or cough greatly increases the chances for infection of the patient's stoma and airway, and may lead to contamination and spreading of infection. Fifthly, in existing products, the pressure over the stoma is not constant and air leaks out during speaking and coughing, the patient thus loses their ability to cough effectively. There is also a risk of Atelectasis (the collapse or closure of alveoli), which can be a consequence of lack of post-expiratory pressure and may affect part or all of a lung resulting in hypoventilation with reduced or absent gas exchange. Atelectasis often correlates with the accumulation of mucus and it may lead to pneumonia in some cases.

Patients in intensive care units (ICU) suffering from critical illness or undergoing major surgery are provided with a tracheostomy tube (TT) if they are expected to require mechanical ventilation for more than about 7 days. A TT makes it easier to wean the patient off mechanical ventilation for a number of reasons. For example, the caregivers can minimize the sedation given to the patient as a TT does not provoke gag reflexes (versus an oral tube). Minimizing the administration of sedatives promotes circulation in the patient. Also, the patient can be active in his own care and mobilization, and awake patients can be participate in pulmonary physiotherapy.

When a TT is removed, the patient is robbed of an ability to provide a vital protection in his airway. The patient is no longer able to create an overpressure in their lungs and chest, which is necessary to clear their airways effectively from secretions/mucus. This is because of air leaking from the stoma. When the patient is weaned from mechanical ventilation they will be equipped with a speaking valve or cap on the tracheostomy tube that will enable them to create a positive pressure (Autopeep) in their chest. The Autopeep (peep is positive end expiratory pressure) is the natural counter-pressure that is created continuously by closing the vocal cords. It is typically a pressure of 5 cm $H_2O$, and during a cough can even be >400 cm $H_2O$ in the chest.

This is important for a number of reasons, including:
the ability to create a voice with successful phonation,
to cough effectively and eliminate secretions,
make deep sighs to open lower parts of the lungs,
prevent atelectasis,
prevent infections—bronchitis and pneumonia, and
maintain sufficient ventilation for oxygen uptake and elimination of carbon dioxide.

The positive pressure is created by a breath/inspiration followed by closing the vocal cords and a relaxed or forced expiration against the closed vocal cords.

With a capped TT the physician or caregiver can also check if the patient's upper airway is free and if they are doing the respiratory work sufficiently well without mechanical help.

When a TT is removed from a patient, they are placed back to a vulnerable situation because there will be an open artificial airway through the stoma, and the patient loses their Autopeep. The typical patient has been ill for weeks, their respiratory muscles are weakened/atrophic, and malnutrition and muscle atrophia are well known results from a long hospital stay.

Although the decannulated patient can breathe/expirate against their closed vocal cords, the maneuver will lack efficiency in the airways due to the opening (stoma) in the front of their neck (the vocal cords are above the tracheostoma).

This situation can be simulated by trying to cough against open vocal cords to feel the inefficiency of such a cough. The strength of the cough will be substantially reduced. The patient's condition may be complicated by weakened respiratory muscles (chest and diaphragm), which may be weakened as a result of mechanical ventilation. During controlled mechanical ventilation the patient's respiratory muscles are moved passively by the pressure from the ventilator/respirator. Any muscle will atrophy by inactivity and the degeneration of muscle tissue may be accelerated by sub-optimal nutrition during a hospital stay. Moreover, the patient will struggle with increased amounts of secretions in their airway due to the newly removed foreign body (TT) and irritated mucous membrane in the trachea wall after numerous suction procedures with catheters, and some patients will even suffer from pneumonia.

When a TT is removed (it is typically a decision by an anesthetist) the stoma/hole will be covered with a bandage. Some caregivers prefer to use an airtight occlusive dressing, which results in a continuous changing of bandages as it will loosen during coughs, talking or pulmonary physiotherapy due to increased pressure from the airway. Secretions from the airway (often infected) will contaminate the front side of the patient's neck. The patient will touch it in an attempt to tidy themselves up, and the majority of the patient group will not have the energy to go and wash their hands afterwards. Typically, the nurse will help the patient with cleaning if they are in the patient room. The nurse will normally try different types of occlusive dressings, and the frequent use and changing of these dressing can lead to excoriation.

Another drawback in relation using an occluding bandage is that secretions will collect and stagnate within the stoma channel, which impedes healing, worsen infection or risk of infection, and a constant flow of air through the stoma disturbs the tissue closing and healing.

Other caregivers acknowledge the above-mentioned challenge and prefer an absorbing non-airtight bandage such as cotton-gauze held in place with skin-gentle tape. This gives the advantage of having absorbing material in a bandage that may be held in place on the patient a bit longer than the airtight dressing as it allows for the passage of air. A disadvantage is that the patient loses their peep unless the bandage is held towards the neck manually. The situation is complicated by the fact that it is not possible to tighten a bandage around the neck as a stoma is located at the very lowest part of the neck.

Some hospitals practice a step-down unit for patients with tracheostomies, which has special skilled nurses and generally a higher staffing compared to normal wards. A general ward has a lower nurse to patient ratio and cannot offer the patient with a tracheostoma optimal help. Studies show that the discharge of a patient with a tracheostomy tube in situ to a ward is associated with increased mortality. The patient is dependent on their assigned nurse, their vigilance and time. The observation and care of a decannulated patient is a challenge as variations in measureable parameters may occur delayed for hours, days, or even weeks. A struggle may be hidden by an increase in inspiration time, respiration frequency, the use of secondary respiratory muscles. Medical notes may report that the patient seem more dyspnea or more labored in his breathing. It is a fact that complications are given more attention when the variation is numerically measureable.

Severe signs of insufficient breathing such as secretion stagnation and need of suction (via nose or mouth, which can be a painful and very unpleasant procedure for the patient), temperature increase, pneumonia, reduced oxygen uptake/reduced oxygen supply to organs, and accumulation of carbon dioxide are all challenges that the newly decannulated patients are facing. The respiratory insufficiency in some cases leads to an unplanned return to the intensive care unit. General deterioration is difficult to separate from the previous clinical picture.

There exists a need for improved treatment of a tracheostoma in a patient.

SUMMARY OF THE INVENTION

According to the present invention, there is provided a device for sealing a tracheostoma in a patient, comprising a seal member for insertion through the tracheostoma to the trachea, which in a first configuration can form a seal by being pulled against the tracheostoma, and which in a second configuration can be removed from the trachea through the tracheostoma.

Preferably, the seal member comprises;

a disc having a predetermined line of weakness, and a first thread attached to the disc, wherein the disc can be broken along the predetermined line of weakness by pulling the thread.

Conveniently, the device further comprises a second thread attached to the disc.

Advantageously, the second thread is attached to the central portion of the disc.

Preferably, the first thread and second thread are different colours.

Conveniently, the first thread passes through the central portion of the disc.

Advantageously, the first thread is attached to a peripheral portion of the disc.

Preferably, the first thread is attached to the central portion of the disc.

Conveniently, the first thread is attached to a peripheral portion of the disc and the second thread is attached to the central portion of the disc.

Advantageously, the predetermined line of weakness is a spiral.

Preferably, the disc is substantially circular Conveniently, the disc is about 20 mm to about 40 mm wide Advantageously, the disc is about 0.5 mm to about 3 mm thick Preferably, the predetermined line of weakness defines a spiral having arms about 1 mm to about 4 mm apart.

Conveniently, the disc comprises silicone, polyvinyl chloride, nylon, polypropylene, polyurethane or PTFE.

Advantageously, the first thread and/or the second thread comprise polypropylene, polyester or polyamide.

Conveniently, the first thread is embedded in the seal member.

Preferably, the device comprises radiopaque material.

According to an aspect of the invention, there is provided a kit for sealing a tracheostoma in a patient comprising a device of the invention and an external cover, the external cover comprising attachment means for the device.

Preferably, the attachment means comprises attachment means for the first thread and/or second thread.

Conveniently, the attachment means comprises a spring, preferably a constant-force spring.

Advantageously, the kit further comprises a tube for inserting the device through a patient's tracheostoma.

Preferably, the kit further comprises instructions for using the device to seal a patient's tracheostoma.

According to an aspect of the invention, there is provided a method of constructing a device of the invention comprising providing a sheet of material, cutting a disc from the sheet, forming a groove to define a line of weakness, and attaching a thread to the disc.

Preferably, the groove is formed by cutting into the material.

Conveniently, the method comprises moulding a disc of material with a predetermined line of weakness and attaching a thread to the disc.

Advantageously, the disc is formed by injection moulding.

Preferably, the disc is formed by polymer casting.

Conveniently, the first thread and/or second thread is attached to the disc in the moulding step.

According to an aspect of the invention, there is provided a method of sealing a tracheostoma in a patient, comprising providing a device of the invention, inserting the sealing member through the tracheostoma into the patient's trachea, and pulling the sealing member to form a seal against the tracheostoma.

Preferably, the sealing member is a disc and has a second thread attached to the disc, and wherein the disc is pulled to form the seal against the tracheostoma by pulling the second thread.

Conveniently, the first thread and/or second thread attached to the disc pass through the tracheostoma and are attached to an external cover.

Advantageously, the external cover applies a tension to the second thread.

Preferably, the second thread is attached to a constant force spring in the external cover.

Conveniently, the method further comprises pulling the first thread to break the disc along the predetermined line of weakness and removing the disc from the patient.

The present invention will now be described, by way of example, with reference to the accompanying figures, in which;

DETAILED DESCRIPTION OF THE INVENTION

Figure 1:
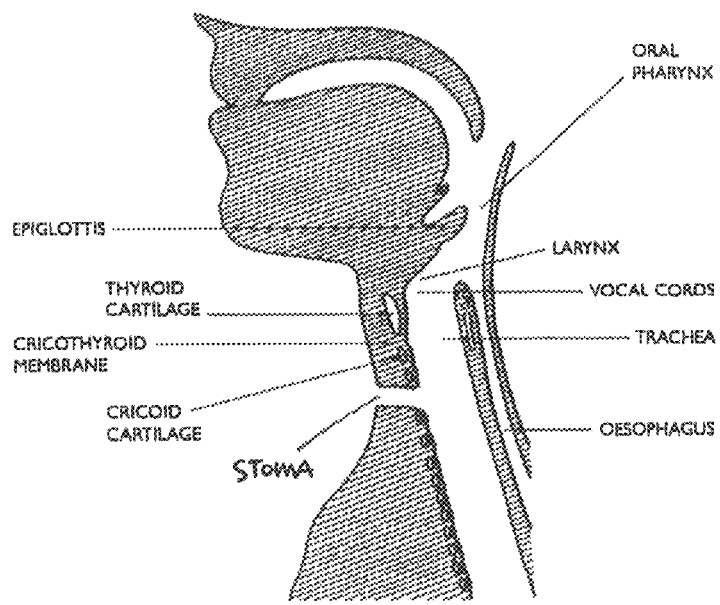
FIG. 1 is a cross-sectional representation of a tracheostoma in a patient.

Turning to FIG. 1, there is a representation of the anatomy of a patient's neck, showing the location of a surgically-created passage (stoma) through their neck into their trachea. This is called a tracheostoma. A tracheostoma is created in many different clinical situations and can provide very good benefits to the patient. The surgical procedure to create a tracheostoma is called a tracheotomy. Typically, when such a tracheostoma is created, a tube is inserted through the stoma to allow for the passage of air in a controlled way (this is termed intubation). After a period of time (such as from one week to several months) the tube is removed. The stoma is then allowed to heal and close. As mentioned above, allowed the passage of air through the stoma can slow down the recovery of the patient and may also create other complications and discomforts for the patient The inventors have found that the healing process can be improved by using a device of the invention to seal the tracheostoma to prevent the unwanted passage of air. After a period of time to allow the stoma to heal and reduce in size, the device can be removed from the patient in a controlled way. In particular, the device can be controllably broken and then removed back through the patient's healing stoma. Typically, the stoma reduces in size as it heals, and the device of the invention is adapted to be removed through such a small hole. This will be explained in more detail below with reference to the figures.

Figure 2:
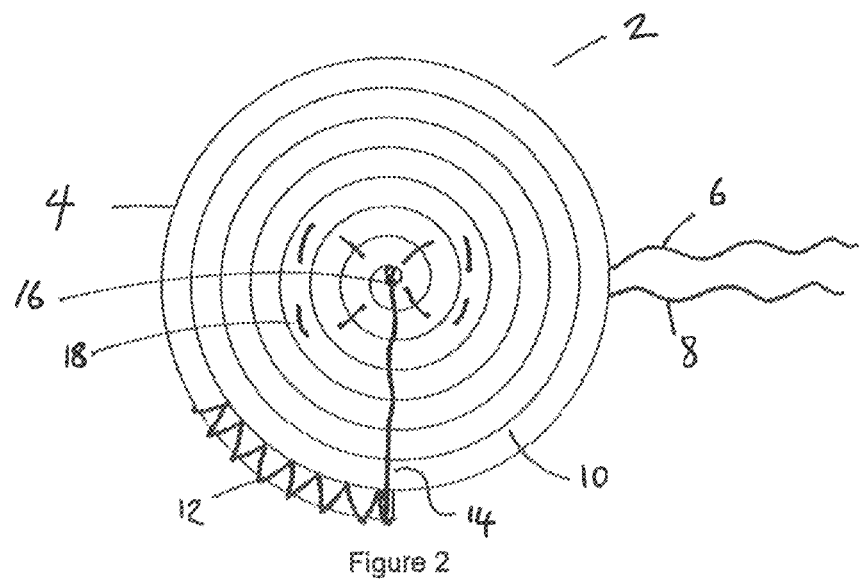
FIG. 2 is a plan view of a device for sealing a tracheostoma.

FIG. 2 shows a device 2 for sealing a tracheostoma in a patient. The device 2 comprises a disc 4 attached to a first thread 6 and a second thread 8. The disc 4 shown in FIG. 2 is of substantially circular shape. Other shapes are contemplated by the invention as long as the disc or disc-like shape is able to be inserted into a patient's trachea and form a seal as will be explained below. Possible shapes include elliptical, ovoid, rectangular, rounded rectangular, square, pentagonal, hexagonal and triangular. Elliptical, and especially circular, shapes are preferred.

The disc 4 is formed of a pliant polymer material which is able to conform and press against the inside of a patient's trachea to form a seal over a stoma, as will be explained below. As shown in FIG. 2, the disc 4 is provided with a predetermined line of weakness 10. In the embodiment shown the line of weakness 10 is formed as a spiral, running from the periphery of the disc 4 to the central portion of the disc 4. In the embodiment shown the line of weakness 10 is created by cutting (scoring) into the material of the disc. Cutting to a depth of about three-quarters of the thickness of the disc 4 is sufficient to create a line of weakness without damaging the structural integrity of the disc 4 or preventing the creation of an effective seal over a stoma. Cutting to other depths is possible, depending upon the material used to form the disc, and how easily the disc breaks along the line.

Typically, for a disc such as that shown in the figures, the force needed to begin unpeeling the disc is between about 6 and 8 Newton. When the disc begins to peel, a lower force is then required, such as between about 2 and 3 Newton to continue and finish the peeling.

The line of weakness may be created in other ways other than cutting, such as creating the line while forming the disc, for example in a moulding step. The line could also be created by using perforation, laser cutting, or the incorporation of another material into the disc. In this embodiment, a cutting filament could be formed in the disc which could be pulled to break the disc in a controlled manner. The broken disc could then be removed from the patient.

It is important for the seal member to be able to be removed safely from the patient. So, it is desirable to avoid unwanted breakage during extraction of the device from the patient. This can be achieved in many different ways. In one embodiment the seal member comprises a thread that is located within or embedded in the material of the seal member. A preferred embodiment of the seal member is in the form of a spiral with a peeling thread attached along the entire spiral. This arrangement has been tested and shown to enable a safe and reliable way to break or unpeel the seal member for extraction. In this arrangement, a user can break the seal member by pulling on the thread, leading to a reliable breaking of the seal member so it can be safely removed from the patient. The thread is preferably embedded in the seal member itself for at least part of the seal member. The thread can be embedded in the seal member along substantially all of the route of the predetermined line of weakness. In the case of a spiral seal member, the thread can be embedded in the material of the seal member along part of or substantially all of the spiral. This arrangement is useful to ensure that the seal member can be securely broken and then unpeeled and removed from the patient.

Although the invention has been illustrated with reference to a disc with a thread or threads, other ways of implementing the invention are contemplated. The invention relates to a device placed into the trachea of a patient which is pulled against the wall of the trachea to form a seal against a tracheostoma, and which may subsequently be removed from the patient through the stoma. The sealing device can be inserted through the patient's tracheostoma and into the trachea, and then can change to a configuration that allows it to form a seal against the tracheostoma. In the illustrated embodiments this takes the form of a disc of material that passes through the stoma in a folded or compressed configuration and then resiliently returns to a more planar unfolded configuration in the trachea.

When it is desired to remove the device from the patient, the device can be removed from the patient by passing back through the stoma. In the situation where the stoma has reduced in size since the introduction of the device, the device can be reduced in size to allow removal. As shown, this can take the form of breaking the disc along a line of weakness to then allow the device to be removed through the tracheostoma.

Other possible ways of implementing the invention are contemplated, so as to allow a device to be inserted through a patient's tracheostoma into their trachea, to form a seal against the stoma, and then subsequently be removed back through the stoma. The formation of a seal involves applying a tension to the device to pull it against the trachea wall to seal the stoma. This is advantageously achieved by attaching the sealing device to an external member (i.e. outside the tracheostoma). The external member can conveniently take the form of a cover placed against the patient's neck in the region of the stoma.

So, the invention in general relates to a device for sealing a tracheostoma in a patient, comprising a seal member for insertion through the tracheostoma to the trachea, which in a first configuration can form a seal by being pulled against the tracheostoma, and which in a second configuration can be removed from the trachea through the tracheostoma.

The sealing member should be able to be inserted into the patient's trachea through a passage no greater than about 9.5 mm. This can be achieved by the sealing member being able to fold up to a shape which fits within this dimension. For example, when a disc is used it can be folded up from a planar shape into a more compressed shape which allows for insertion through the tracheostoma. Once inside the trachea, the sealing member can then assume a first configuration which allows it to form a seal against the tracheostoma. For a disc-like member, this can be achieved by the use of resilient material which ensures that the disc unfolds into a more planar shape once inserted into the trachea, which is wider than the stoma.

When it is desired for the sealing member to be removed, it is converted to a second configuration which allows it to be removed from the stoma, which is often substantially smaller than the initial size of the stoma. So, for example, the sealing device may need to be removed through a passageway about 3 mm wide. In the case of a disc-like device, it can be split or broken into a second configuration which allows it to be removed through such a small channel. The disc can be unpeeled or unravelled so it can be withdrawn through the healing stoma.

In some embodiments the depth of the cut forming the line of weakness can vary along the length of the line. So, it may be preferable for the line of weakness to be stronger at the point where the disc would begin to break (at the periphery in the embodiment in FIG. 2), so as to prevent unwanted premature breaking of the disc. This arrangement would require a higher force to begin breaking the disc, and a subsequent lower force to continue breaking or unravelling the disc.

In some cases it may be preferred to make the line of weakness stronger (harder to break) where a thread applies tension to the disc (for example at the centre of the disc). So, in embodiments where a thread is attached and is used to pull the disc to form the seal, it is preferred for the line of weakness in the area that the thread is attached to be stronger (more resistant to breaking) than elsewhere. This reduces the risk of premature breaking of the disc.

In some situations it may be preferable to introduce the device into patients by using an introducer tube or sheath. In this sort of situation it is beneficial to store the seal member on a flat or relaxed state while in storage, rather than being kept folded or compressed in the introducer tube while in storage. Keeping the seal member folded or bent for a long time may cause it to be damaged or may prevent it from fully unfolding in the patient, and so may prevent an optimum seal being formed. Instead it is preferred to keep the seal member in a flat or relaxed state during storage (potentially for a relatively long period of time) and then be folded up at the time that it is needed to be inserted into a patient. For example, the device could be made ready for use at the time that it is needed by the user carefully pulling on the tension thread to draw the seal member into the insertion sheath.

To facilitate being inserted into place in a patient, the device could have an edge which is straighter than a round or elliptical shape. So, when folded or rolled up for insertion via an introducer sheath or the like, the seal member could present a substantially flat edge which can more easily be pushed against.be more square than it is now, which would facilitate its physical introduction into patients.

For some patients, for example children, small adults or overweight patients with an increased depth of pretracheal tissue, it may be more beneficial to use a guide wire rather than an introducer sheath. Conventional surgical techniques could be used to introduce a guidewire leading to the correct position for the seal. For example, a guidewire could be inserted through the tracheostomy tube being removed in the decannulation procedure. An insertion plunger with a groove on its outside could then be used, which would allow the plunger to follow the guide wire when located in the groove to help guide the introduction of the device. A guidewire can also be used in non-surgical techniques to introduce the seal device. In one aspect, a guidewire can be used to help guide an insertion sheath into the correct position to insert the sealing member into the patient.

The disc 4 comprises silicone polymer, formed by cutting the disc shape from a sheet of silicone polymer and cutting the line of weakness using a plotter fitted with a knife. This method enables very good control over the shape of the disc, and the shape and depth of the scored line of weakness. The material used was a sheet of silicone 1.0 mm thick (sold by AAG Aalborg Gummivarefabrik A/S as silicone SST601T).

The illustrated disc was been made by cutting out a disc from a sheet of silicone on a Leica WILD TA30 precision plotter. The pattern of grooves were cut first with low pressure on a knife, making a cut only three quarters through the material. This method is very useful due to its high precision and ease of changing the setup of the cutting.

In the embodiment shown, the line of weakness 10 is in the form of a spiral extending from the centre of the disc 4 in a progressive concentric manner to the periphery of the disc. The disc 4 shown has the line 10 in the general form of an arithmetic or Archimedean spiral shape, such that the radial distance between adjacent arms of the spiral is substantially constant. Whilst this form of spiral is preferred, other forms are acceptable as long as they allow for the controlled breaking of the disc along the line of weakness. Although the use of one line of weakness is preferred, it is possible to include more than one line of weakness, such as two lines of weakness.

For the disc shown, the material has a thickness of 1.0 mm. The spiral has a pitch of 2 mm from the periphery to the centre. At the centre of the disc the last turn of the spiral has a pitch of 1.5 mm. The disc has a diameter of about 26 mm.

An alternative method of producing the discs is by injection moulding. In this case, the grooves in the disc would be made by patterns in the tool. The discs could be made by injection moulding a thermoplastic material. Another option is to use materials that polymerise in situ in the mould to form the disc, such as a two-component silicone system. Both systems could produce discs to which are attached the thread or threads in a subsequent step, for example by stitching.

Another way to attach the strings to the disc is by embedding them in the disc when this is made. The strings would be held in place in the moulds and the disc material would be inserted. This process called Insert Moulding. The disc could be made of different materials, for example silicone could be used. Here a two-component silicone liquid would be required. Thermoplastic materials could also be used, allowing injection moulding, a process very suited for large quantities.

Techniques which allow for a thread to be incorporated into the device can result in a strong attachment of the thread with the material of the disc. This attachment may be strong enough so that further securement means are not needed. In some cases, however, it may be preferred to combine the insertion of the thread into the material of the disc with another securement method, such as additional sutures, to ensure the thread is strongly fixed in place.

Preferably the disc is substantially planar. In other words, the disc is flat or planar when no forces are being applied to it. It is preferred for the disc of the material to be unitary, i.e. to be formed from a single piece of material.

The disc can be any appropriate size to seal a stoma. Although the device can be used in animals, the patient is preferably a human. The disc may be from about 20 mm to about 40 mm wide, more preferably from about 20 mm to about 30 mm The disc is preferably from about 0.5 mm to about 3 mm thick, more preferably from about 0.8 mm to about 1.5 mm thick, more preferably about 1 mm thick.

The predetermined line of weakness preferably defines a spiral having arms about 1 mm to about 4 mm apart, more preferably about 1.5 mm to about 3 mm wide, more preferably about 2 mm wide.

The disc preferably comprises silicone, polyvinyl chloride, nylon, polypropylene, polyurethane or PTFE, more preferably silicone.

Using insert moulding also opens for the possibility of using other types of thread or string. An important issue when considering insert moulding the thread is how to make a strong bond between the thread and the disc. There are basically two methods, chemical bonding or a mechanical bonding. Chemical bonding requires the thread material and the disc material to be compatible, which limits the number of combinations of material. A monofilament string could be used if a chemical bond is present. Placement of a string, with chemical bonding to the disc, in the mould would not necessitate the string be held in the middle of the cavity. The string would adhere to the disc even if only half embedded in the disc.

A mechanical bonding can be achieved by interlocking the materials, the materials must flow through each other, preventing them from being pulled apart. A woven string, which has a larger surface, compared to a monofilament string, would allow a good chemical bond and the gaps between the single strands would allow a mechanical bond. The bigger the gaps between the strands of a string would be, the greater the mechanical bonding, the disc material would easily flow through the string and fill the gaps.

Another option is to make an extruded version, where the thread or threads are over-moulded with a thermoplastic polymer and then rolled up in spiral, before it gets a heat treatment to get it in the shape of the disc.

As mentioned, the disc 4 is attached to a first thread 6 and a second thread 8. In this embodiment, both threads comprise conventional surgical suture material, namely a polyester filament (sold by Johnson & Johnson as Mersilene® suture material). Many other types of thread can be used. The material needs to be compatible for use in this clinical situation, and needs to retain structural strength for extended periods of contact with the patient's body. The material also needs to be able to be sterilised for medical use, for example by steam autoclave, treatment with ethylene oxide or by radiation sterilisation.

Many conventional suture materials are acceptable for use, such as polypropylene, poly(hexafluoropropyle-VDF), polyester and polyamides (such as nylon).

In general, the word "thread" as used herein refers to a member which is attached to the disc and which can pass out of the patient's stoma, and which can be used to apply tension to the sealing member (e.g. a disc) to form the seal. Such a member need not comprise thread as such, and so may comprise any suitable material or structure other than those used in surgical sutures. So, the term "thread" can also mean material such a polymer filament, a metal wire, a silk thread, a thin strip of material, a multifilament thread, braided or woven materials and so on. In some embodiments the thread can comprise the same material as the sealing member itself, and/or may be unitary with the sealing member.

In order for caregivers to be able to easily distinguish the first thread 6 from the second thread 8, the threads in the illustrated embodiment are different colours. Other ways of distinguishing the threads apart are acceptable. In addition to, or as an alternative, labels or other indicia may be provided on the threads to ensure that users can distinguish between them and so use the device correctly.

The first thread 6 passes through the centre of the disc 4 and then extends generally radially towards a peripheral portion of the disc 4. FIG. 2 shows a portion 14 of the first thread 6 which extends from the centre of the disc 4 to the periphery of the disc 4. The first thread 6 is attached to the end of the spiral arm formed by the line 10, extending for along a portion of the periphery of the disc 4, attached by a number of sutures 12. The sutures 12 are intended to create a strong attachment of the first thread 6 to the material of the disc 4 at the point where it is intended to begin to break the disc 4.

The stitching of the threads can be done by hand, which allows for a high precision and ease to change the configuration of the stitching scheme. The stitching can also be up-scaled to an automatic production line, where the stitching is done by an embroidery machine or similar automatic sewing machine.

Looking back to the centre of the disc 4, there is provided a knot 16 in the first thread 6 at the point where the first thread 6 emerges after passing through the material of the disc 4. Another knot 20 (not visible in FIG. 2) is provided in the first thread 6 in a similar position on the underside of the disc 2. The purpose of the knots 16 and 20 is to hold the relative position of the first thread 6 fixed in relation the disc 4 while the device is deployed in the patient. This is to prevent unwanted premature movement of the first thread 6 and potential breaking of the disc 4.

There is also a second thread 8 attached to the disc 4. The second thread 8 is attached at the central portion of the disc 4 by a series of wide sutures 18 spread around the central portion of the disc 4. Unlike the first thread 6, the purpose of the second thread 8 is not to cause the disc 4 to break along the line of weakness 10. Instead, the purpose of the second thread 8 is to apply tension (pulling force) to the disc to hold it in place to form a seal against a patient's stoma. This will be explained below in more detail.

So, the second thread 8 is attached around the central portion of the disc 4 in a way intended to spread the tension across a relatively large area to avoid breaking the line of weakness or otherwise tearing or breaking the material of the disc. To this end, it is preferred to use thicker filaments which can spread force more effectively.

Figure 3:
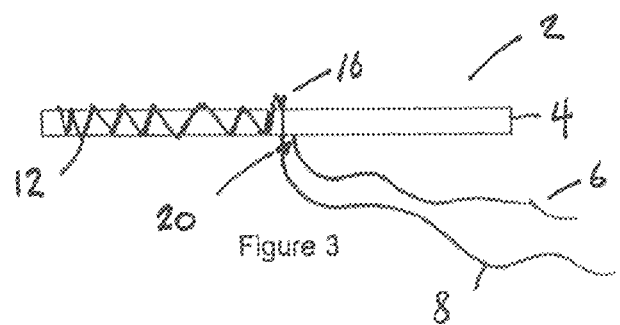
FIG. 3 is a side view of a device for sealing a tracheostoma.

Turning now to FIG. 3, a side view of the disc 4 is shown, showing how the first thread 6 and second thread 8 are attached and extend away from the central portion of the disc. The knots 16 and 20 in the first thread 6 can be seen on either side of the disc 4.

Figure 4:
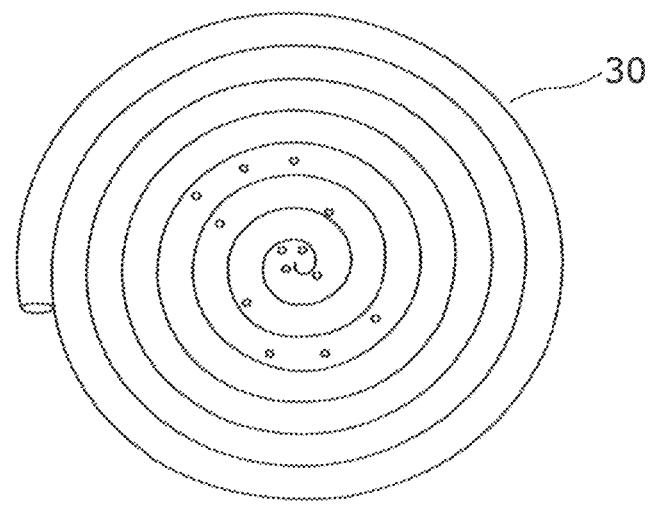
FIG. 4 is a photograph of a partially constructed device for sealing a tracheostoma.

FIG. 4 is a photograph of a disc 30 in the process of being constructed. The disc 30 has been cut out from a sheet of silicone polymer material and has a line of weakness scored through three-quarters of the thickness of the material using a computer-controlled plotter. The intended location of the suture locations for threads has been marked on the disc 30.

Figure 5:
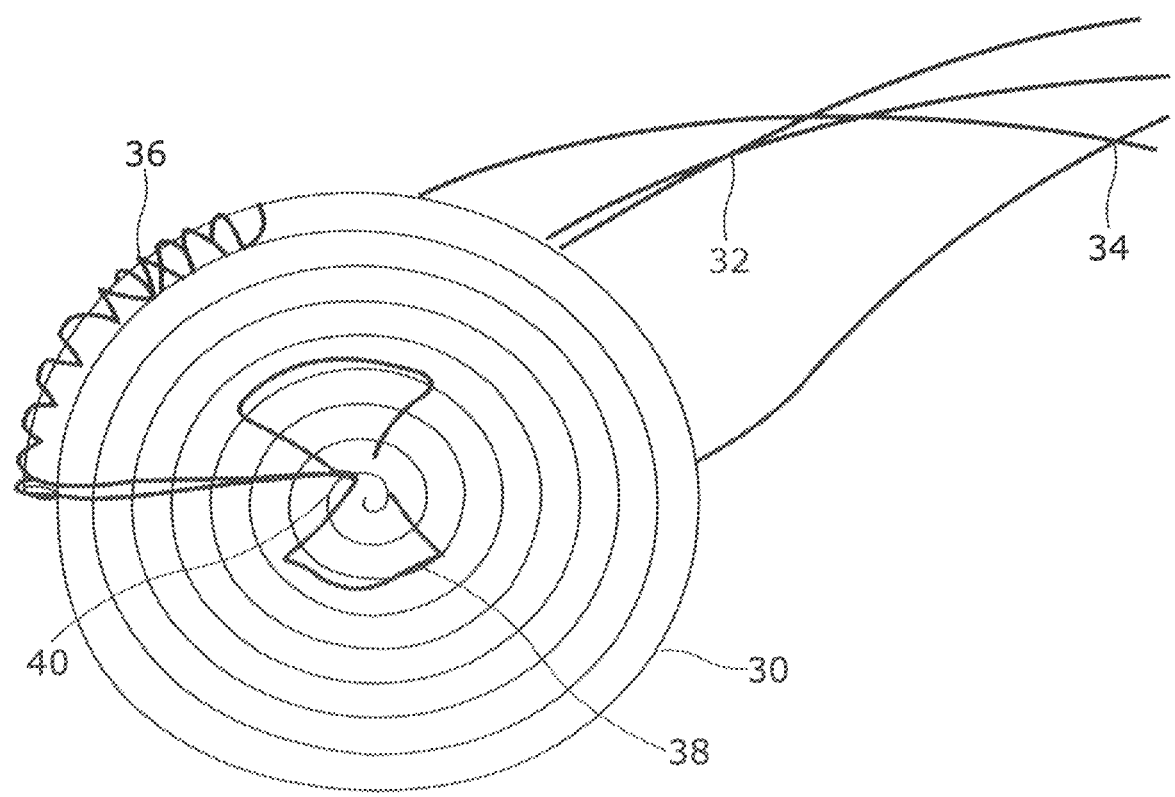
FIG. 5 is a photograph of a device for sealing a tracheostoma.

FIG. 5 shows the disc 30 after the attachment of a first thread 32 and a second thread 34. The first thread comprises a loop of Mersilene® polyester filament which passes through the centre of the disc 30, with a knot 40 being positioned on the thread 32 just above the centre of the disc. Another knot (not visible) is positioned on the thread 32 just below the centre of the disc, to keep the position of the first thread 32 fixed until the controlled breaking of the disc occurs.

The first thread 32 passes from the centre of the disc 30 to the periphery, and is attached to the distal end of the spiral shape of the disc along the edge of the disc by a series of sutures 36.

The second thread 34 again comprises a loop of Mersilene® polyester filament which is attached to the central portion of the disc 4 by a number of sutures 38 extending around the central portion of the disc 30.

We will now explain how the device of the invention is used to seal a tracheostoma in a patient, and is then removed some time after. In general, the device is inserted through the tracheostoma and into the patient's trachea, and is then pulled against the wall of the trachea to form a seal. The seal prevents the passage of air through the stoma, thus aiding the healing and recovery of the patient and the stoma.

Figure 6:
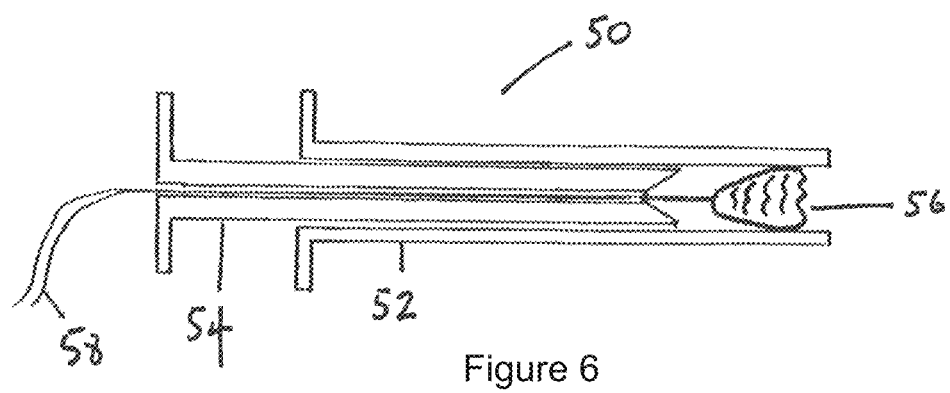
FIG. 6 is a cross-sectional view of a device for sealing a tracheostoma loaded into an insertion sheath.

It is preferable to use an insertion device to assist in the effective insertion and deployment of the sealing devices of the invention. FIG. 6 shows a syringe-like insertion sheath 50 which is used to deploy a sealing device 56 of the invention in the patient. The insertion sheath 50 comprises an outer barrel 52 and an inner sliding plunger 54. The plunger 54 has a channel running along its length and is slidably positioned within the outer barrel 52.

In use, a sealing device 56 is folded and inserted into the distal end of the barrel 52, with the attached threads 58 passing along the length of the insertion sheath 50, through the channel passing through the plunger 54. The sealing device is now ready to be deployed in a patient.

The insertion sheath 50, and particularly the outer barrel 52, are made of material compatible for contact with the patient. For example, the insertion sheath 50 may comprise material used for construction of intubation devices which are used for insertion into a patient's tracheostoma. At least the distal end of the barrel 52 is constructed of a material which is sufficiently rigid to hold its shape when holding the sealing device 56, i.e. to resist being deformed outwardly by the pressure of the folded sealing device 56.

In the embodiment shown, the barrel is made from PTFE and has a length of about 76 mm and an internal diameter of about 8 mm. The plunger fits within the barrel to give a close fit that allows the plunger to be moved axially along the length of the barrel. The plunger has an internal open channel of about 5 mm diameter.

Figure 7:
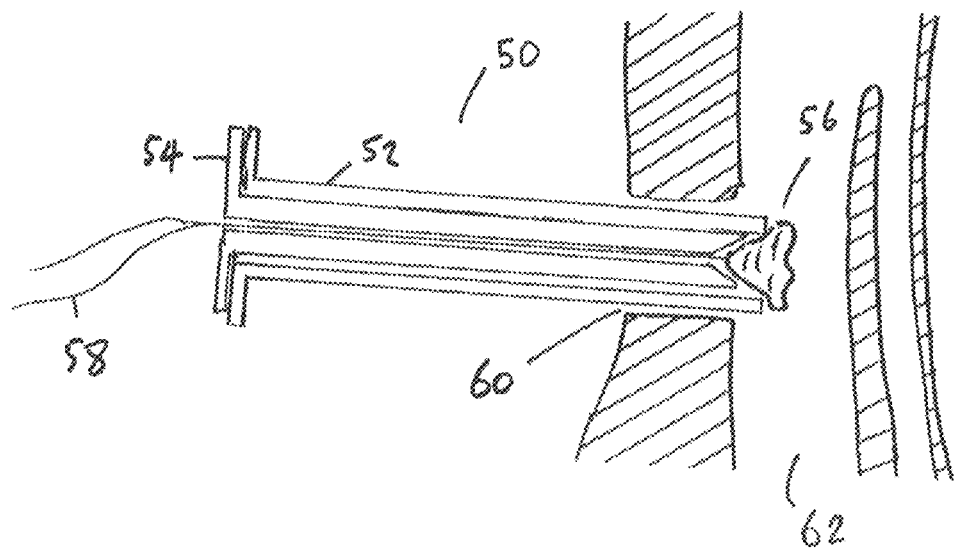
FIG. 7 is a cross-sectional view of a device for sealing a tracheostoma being inserted through a patient's stoma.
Figure 8:
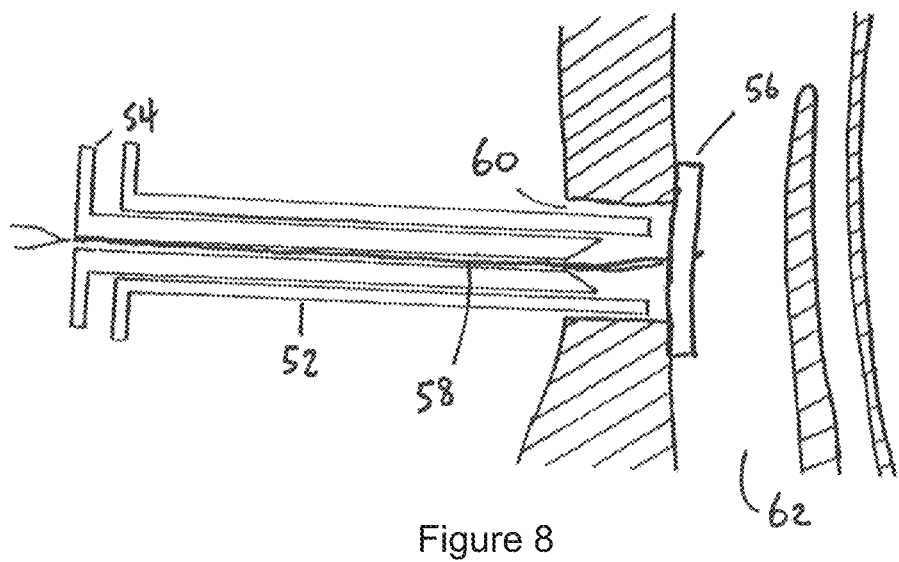
FIG. 8 is a cross-sectional view of a device for sealing a tracheostoma being deployed into a patient's trachea.

As shown in FIG. 7, the insertion sheath 50 is then carefully inserted into the patient's tracheostoma 60, so that the distal end of the barrel 52 extends into the patient's trachea 62. According to the preference of the caregiver, the insertion and deployment process can be monitored to ensure correct placement. This can be achieved, for example, by the use of an endoscope to visually assess the location of the insertion sheath 50 and sealing device 56. Other monitoring methods could be used. In some embodiments the insertion device or the sealing device, or both, comprise radiopaque material, so that their location can be determined fluoroscopically.

Once the distal end of the barrel 52 is in the correct position, the plunger 54 is pushed forwards to push the sealing device 56 out of the distal end of the barrel 52. FIG. 7 shows the sealing device 56 being pushed out of the barrel 52 into the patient's trachea 62.

After the sealing device 56 has been pushed out of the barrel 52, it resiliently expands to return to a substantially planar disc-like shape. This is due to the elastic, resilient nature of the material used to form the disc of the device 56. The disc 56 is wider than the stoma 60 in the patient's trachea. The insertion device 50 can then be withdrawn from the patient's stoma.

Figure 9:
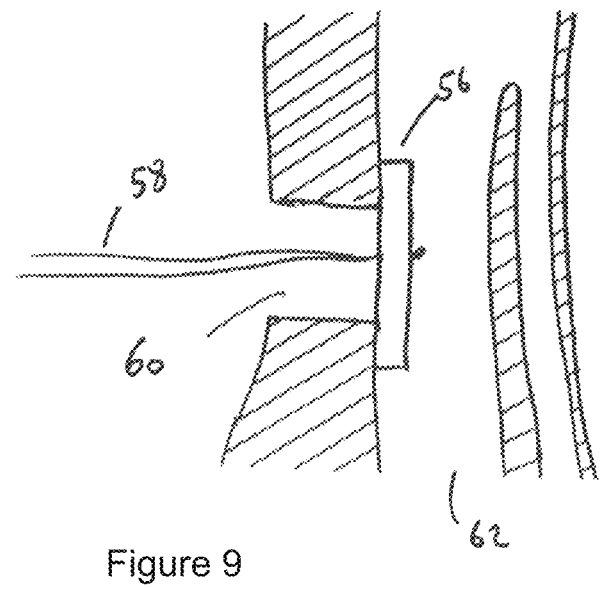
FIG. 9 is a cross-sectional view of a device for sealing a tracheostoma deployed next to a patient's stoma.

FIG. 9 shows the resulting situation with the sealing device 56 successfully deployed into the patient's trachea. Tension is then applied to a thread 58 attached to the disc of the device 56 to pull the disc against the wall of the trachea around the location of the stoma 60. The compliant nature of the material used to form the disc of the device 56 ensures that it forms an effective seal around the stoma. This seal effectively prevents the unwanted passage of air through the stoma, to allow for healing and recovery.

The wall of the trachea wall is covered by motile cilia which move and facilitate the movement of mucus. The function and health of the cilia depends critically on the temperature and humidity of the inhaled air. The air flowing through a stoma is drier and at a lower temperature than the normal, optimum conditions, and damages the cilia and their function. It is helpful for the health and recovery of the patient to seal their stoma and re-establish the optimum conditions in the trachea for the cilia to function, and to prevent the unwanted passage of air and secretions. The invention is able to provide a good seal and so can further aid in the recovery of the patient.

Figure 10:
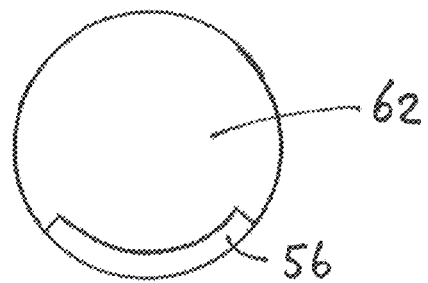
FIG. 10 is a schematic plan view of the situation shown in FIG. 9 of a device for sealing a tracheostoma deployed inside a patient's stoma.

FIG. 10 shows a representation of a view looking down the patient's trachea 62, showing that the disc of the sealing device 56 has pressed against the wall of the trachea to form a seal. The material and dimensions of the disc of the device 56 allow it to flexibly confirm to the shape of the wall of the trachea 56 to form a seal around the stoma 60.

Figure 11:
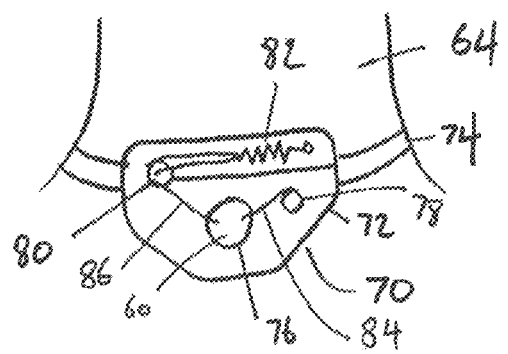
FIG. 11 shows an external cover worn by a patient to hold the device for sealing a tracheostoma in place.

FIG. 11 shows an external cover 70 which is placed on the outer surface of the patient's neck 64 at the location of the stoma 60. The external cover 70 comprises a housing 72 which has an aperture 76 located above the position of the patient's stoma 60. As shown a first thread 84 and a second thread 86 are attached to the sealing device and pass through the stoma 60 and through the corresponding hole 76 in the housing 72 to the outside of the patient's body. The cover 70 is kept in place by a strap or bandage 74 passing around the patient's neck.

The first thread 84 is loosely but securely attached to the cover 70 by a screw clamp 78. This results in the first thread 84 being securely connected to the cover 70 without excessive tension being applied to the thread 84 which could otherwise cause premature breaking of the device.

The second thread 86 is passed around a low-friction member 80 of the housing and is then connected to a spring 82 before looping back to be secured to a screw clamp on the member 80. This arrangement is designed to ensure that a controlled amount of tension (pulling force) is applied to the second thread 86, and so to the disc of the sealing device. This tension ensures that the disc is always pulled against the wall of the trachea to maintain an effective seal of the stoma. It is preferred that the pressure of the device against the wall of the trachea is not more than about 25 mm Hg. A higher pressure against the trachea may lead to damage to the tissue, especially for longer periods of time.

Various types of spring may be used to provide tension, such as a helical spring. Various materials may be used for the spring, such as plastic materials and metals such as steel, preferably stainless steel.

A preferred spring is a constant-force spring. A constant-force spring is a spring for which the force it exerts over its range of motion is a constant. That is, it does not obey Hooke's law. Generally constant-force springs are constructed as a rolled ribbon of spring steel such that the spring is relaxed when it is fully rolled up. As it is unrolled, the restoring force comes primarily from the portion of the ribbon near the roll. Because the geometry of that region remains nearly constant as the spring unrolls, the resulting force is nearly constant.

FIG. 11 shows the use of a single spring in the external cover. More than one spring may be used, such as two springs. Where two threads are used, it is possible to use a single spring on the thread required to provide tension on the seal. It is also possible to use a spring for each thread to apply tension to the threads.

This arrangement allows for the distance between the inner wall of the patient's trachea and the outer surface of their neck to change, which can happen as the patient moves, especially from a supine to an upright position. The constant-force spring allows for some change is distance whilst keeping the tension applied to the disc of the sealing device relatively constant.

Figure 12:
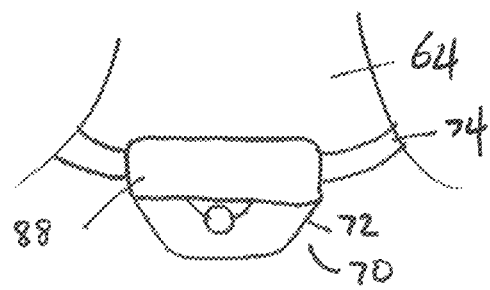
FIG. 12 shows the external cover of FIG. 11 covered by a lid.

FIG. 12 shows the finished situation after the insertion of the sealing device has been completed. Once the caregiver has secured the threads to the housing 72, a lid 88 is removably attached to the housing 72. The lid 88 keeps the threads secure and prevent inadvertent or unwanted premature unravelling of the sealing device. The lid 88 also prevents potentially dangerous loosening of the tension keeping the disc in place. Inadvertent loss of tension in the second thread 86 could cause the disc to move from its position against the wall of the trachea.

This could remove the seal from the stoma and, more seriously, could cause a blockage in the trachea itself.

The housing and lid of the external cover can made by a SLS printer (Selective laser sintering), although other additive manufacturing (3D printing) techniques would be acceptable. SLS is preferred because it offers a sufficient degree of detail and strength, considering the application. Furthermore it is possible to print in a material suited for implanting in an organism, in this case PA 2200, a polyamide.

For production of large numbers of devices another production method than 3D printing is preferred, such as injection moulding. Injection moulding is a suitable production method when large quantities are needed.

A material should be chosen for its suitability for applications in the healthcare sector and for good mechanical properties. Suitable materials include medical approved ABS (Acrylonitrile butadiene styrene). This material has many attractive attributes, as it can be welded or glued together and combined with other materials in insert moulding.

A constant force spring is preferred for use in the device of the invention. A spring with 200 mm extension would be suitable. This extra extension could be used for pulling the external device out from the patient's neck and thereby allowing a nurse to clean the wound, while the spring would keep the same pull force on the disc.

The stoma is located quite low on the patient's neck and this can make it difficult to secure a cover over the area of the stoma. Preferably the external cover is constructed to allow it to bend or fold to confirm better to the shape of the patient's neck. For example, the cover may allow bending around the central axis so that each side of the cover can move back to contact the patient's neck on each side of the stoma. The cover could have a V-shape to better confirm to the low position of the stoma on the patient's neck. The V-shape of the cover can be adjustable to allow a good fit for the patient. This allows the cover to be attached more securely in place with a strap or bandage passing around the back of the patient's neck.

The sealing device can be provided as a kit, along with means for inserting the device into patient. It is convenient for a sealing device to be provided together with an insertion sheath, sterilised and ready to be opened and used by a caregiver. The kit can also include instructions for inserting the device and for removing the device. Preferably, the kit can comprises a guide wire that can be inserted into a TT that is being removed. The insertion means for the sealing device can then be inserted along or over this guide to facilitate insertion into the tracheal lumen. This technique is preferred in some patients. For example, a blind insertion in obese patients can be a challenge as the different layers of tissue often will move. Using a guide, for example the distal part of a suction tube (plast), is a common tool in this procedure when the clinician wants to change a tracheostomy tube. A metal guide wire with a soft tip may also be suitable. Displacement of a tracheostomy tube is also known as creating a via false.

The sealing device of the invention gives the wound peace to heal over a few days. The sealing of the stoma protects new granulating tissue from germ/microorganisms, from airway mucus and from the surrounding environment.

There should be a tension between the external fixation and the internal sealing that minimizes passage of air and secretion, and the tension should allow the caregiver to change an absorbing bandage underneath the external fixing element if required.

With the sealing device in situ the patient regains the ability to generate intrathoracic pressures that are needed to generate the requisite expiratory flows and airstream velocity in a phase after critical illness or major surgery, an ability to create autopeep opens the peripheral parts of the lung/alveoli that means a better ventilation, exchange of oxygen and carbon dioxide is possible.

Once the sealing device has been placed in the patient to form a seal, the patient is allowed time for the stoma to begin to heal. For most patients, the stoma will heal and reduce in size over a number of days. After a period of, for example, one to two weeks, the stoma will have healed enough to allow the sealing device to be removed. As a stoma heals it generally reduces in size, so that the hole through which the sealing device is to be removed is smaller than the hole through which is was introduced.

The design of the sealing device of the invention allows for the controlled breaking of the disc, which reduces the size of the device to allow it to be removed through the patient's stoma. This process will be explained showing the sealing device alone, and then showing the device in situ in a patient's body.

Figure 13:
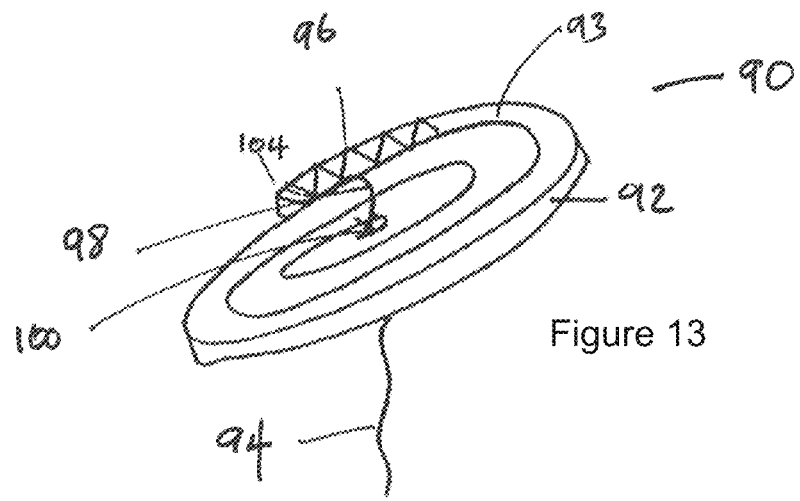
FIG. 13 is a perspective view of a device for sealing a tracheostoma having an attached thread.

FIG. 13 shows a sealing device 90 comprising a substantially circular disc 92. The disc 92 has a predetermined line of weakness 93 in the form of a spiral running from the periphery to the centre of the disc 92. The line of weakness 93 is formed by cutting through a portion of the thickness of the disc 92. A thread 94 extends though the centre of the disc 92 from one side to the other. A knot 102 is located on the thread 94 on the underside of the disc 92. Another knot 100 is located on the thread 94 on the upper side of the disc 92. The knots 100 and 102 are intended to substantially fix the relative position of the thread 94 to the disc 92 while the device is being deployed and used.

Other means for temporarily fixing the position of the thread are possible, such as the use of small beads or dabs of adhesive on the thread to create physical resistance to movement of the thread through the disc.

After passing through the centre of the disc 92, a portion 98 of the thread 94 extends out to the periphery of the disc 92 and is securely attached to the distal portion 104 of the spiral arm of the disc 92 by a number of sutures 96.

Figure 14:
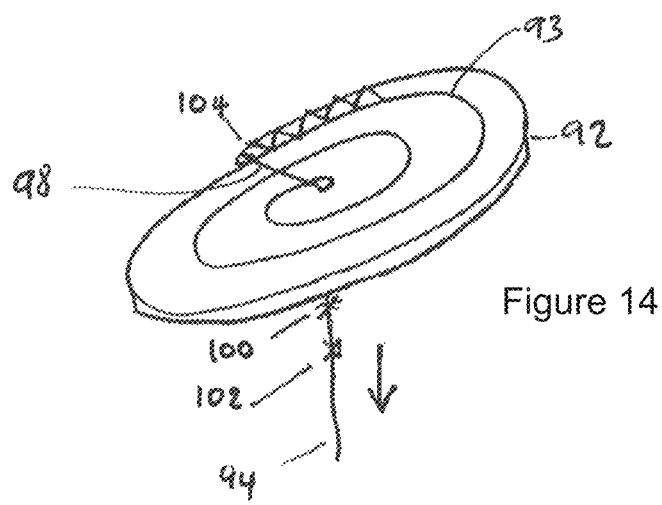
FIG. 14 shows the device of FIG. 13 with the thread being pulled.

When a caregiver wishes to remove the sealing device 90 from within the patient's trachea the following procedure can be followed. The thread 94 is carefully pulled by the caregiver. This results in the thread 94 being pulled taut, with further movement being prevented by the resistance of the knot 104 being pulled up against the surface of the disc 92. The caregiver can then pull the thread 94 slightly harder until the knot 104 is pulled through the centre of the disc 92, which then pulls the portion 98 of the thread 94 taut. This leads to the position shown in FIG. 14.

Figure 15:
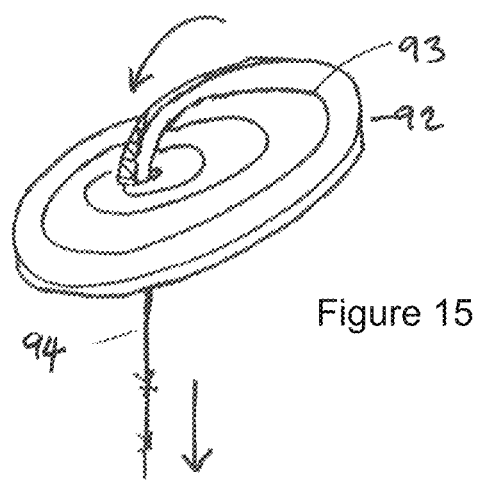
FIG. 15 shows the device of FIG. 14 being broken along a predetermined line of weakness.

Further tension applied by the caregiver will apply force to the distal end 104 of the spiral arm of the disc 92. This causes the disc to begin to break along the predetermined line of weakness 93 at the distal end 104 of the disc 92. As the caregiver continues to pull the thread 94, the disc is progressively split along the spiral line 93, pulling the distal end 104 of the spiral arm of the disc 92 towards the centre of the disc 92, leading to the situation shown in FIG. 15.

Figure 16:
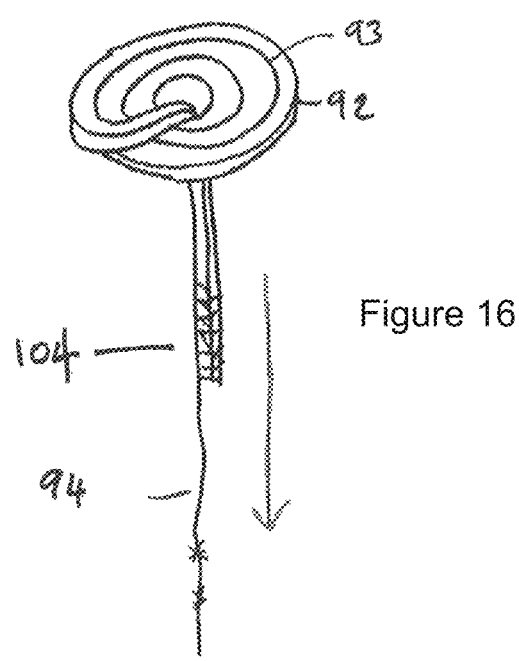
FIG. 16 shows the device of FIG. 15 being further broken and unravelled.

Further tension causes the unravelled end of the disc to be pulled through the centre of the disc 92, and then out of the stoma of the patient. This situation is represented in FIG. 16. As the caregiver continues to pull on the thread 94, the disc continues to be unravelled along the line of weakness 93, and be pulled out of the patient. This unravelling or peeling of the disc of the device continues until the remainder of the disc is small enough to pass through the stoma. The patient can then be treated in a conventional way now that the stoma has reduced in size.

Figure 17:
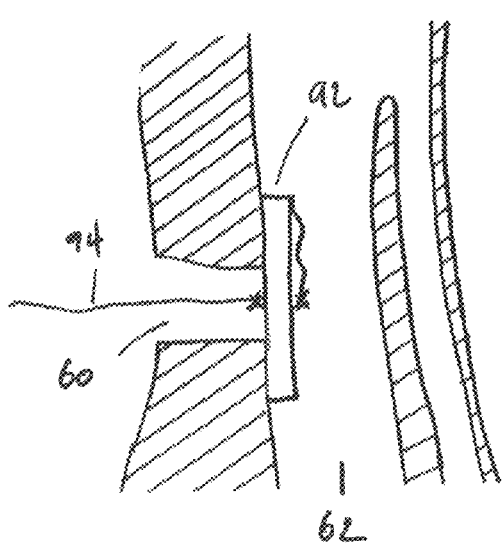
FIG. 17 is a cross-sectional representation of a device in place sealing a patient's tracheostoma with an attached thread.

The removal process will now be discussed with reference to FIGS. 17 to 21 which show the device in situ. FIG. 17 shows a disc 92 in place within the patient's trachea, forming a seal against a stoma 60. Slight tension is being applied to the thread 94 extending from the disc 92 out of the stoma 60 to keep the seal in place.

Figure 18:
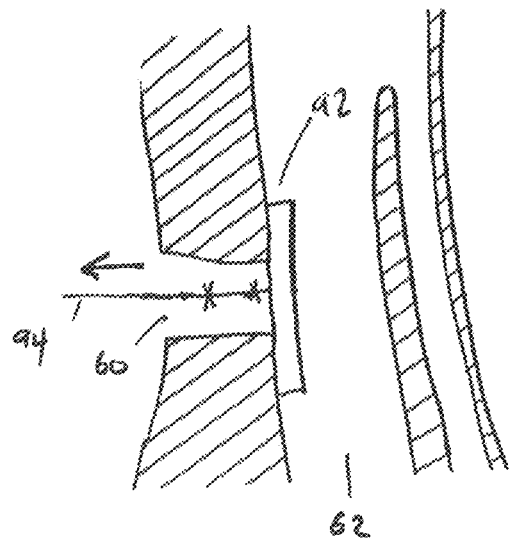
FIG. 18 shows the device of FIG. 17 with the thread being pulled taut.

When the caregiver applies more force, the thread 94 is pulled so that the knot on the far side of the disc is pulled through the centre of the disc. This gives tactile feedback to the caregiver of the progress of the removal process, and is shown in FIG. 18.

As the caregiver continues to pull on the thread 94, the disc beings to break along the predetermined line of weakness. As this process continues, the end of the spiral defined by the line is pulled towards the centre of the disc, resulting in the situation shown in FIG. 19.

Figure 20:
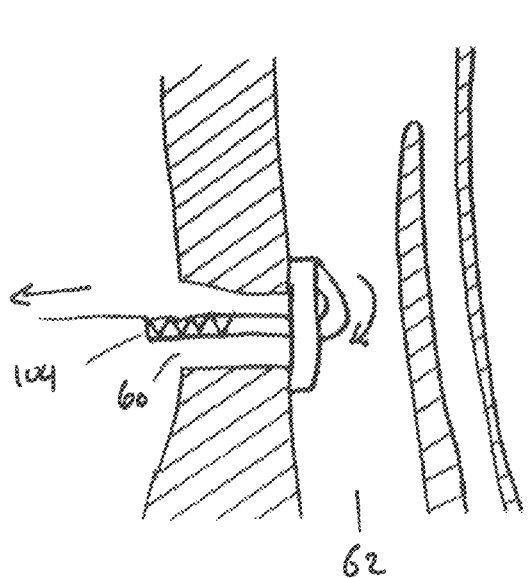
FIG. 20 shows the device of FIG. 19 being further unravelled along the line of weakness.
Figure 19:
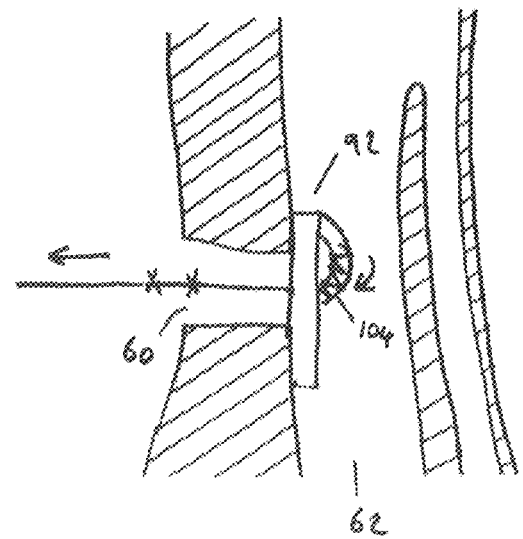
FIG. 19 shows the device of FIG. 18 beginning to be unravelled along a line of weakness.

Further pulling of the thread forces the unravelled end 14 of the spiral of disc material to be pulled through the centre of the disc 92 and out of the stoma 60, as shown in FIG. 20.

The sealing device of the invention can function with a single thread. That is, a single thread can perform both functions of applying tension to the disc to keep it in place to seal the stoma, and also to serve to break the disc along the line of weakness. In order for a single thread to perform both functions it is important to be able to apply the required level of tension to keep the seal in place without undue risk of unwanted premature breaking of the disc. This could be achieved in similar way to the use of the knots (or other physical resistance arrangement). This would allow a first level of force to be applied to the thread to keep the seal in place, and would require a second, higher level of force to the applied to the thread to cause the disc to break along the line of weakness.

It is preferred that the disc has two threads, rather than one, with a first thread being used to apply tension to the disc to keep the seal in place, and a second thread being used to break the disc along the line of weakness.

The illustrated embodiments show a disc that unravels from the outer portion of the disc. However, it is possible for the disc to unravel from the central portion instead. So, a thread could be attached to the centre of the disc which, when sufficient tension is applied, causes the line of weakness to split the material of the disc from the centre outwards. This arrangement is preferred if a single thread is used.

Figure 21:
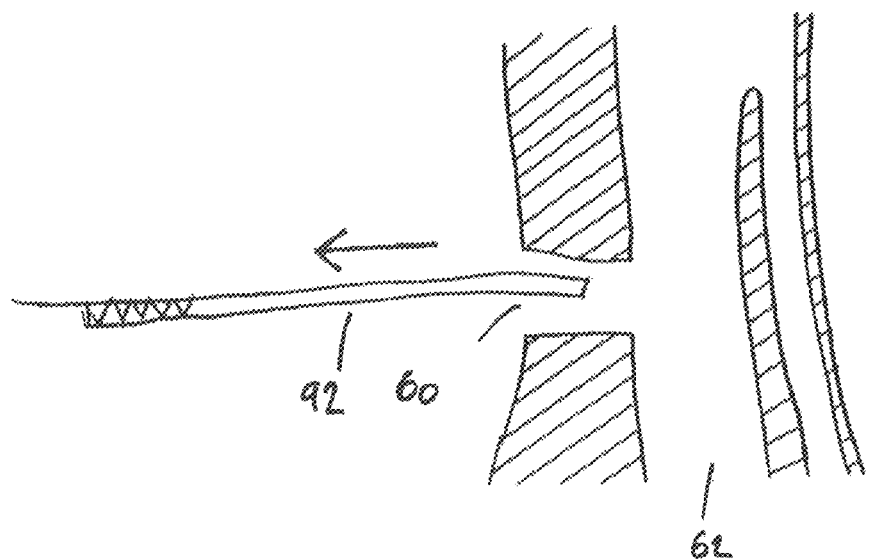
FIG. 21 shows the unravelled device of FIG. 20 being removed through the patient's tracheostoma.

As explained above, this process continues until the size of the remainder of the disc 92 is small enough to be pulled through the patient's stoma and out of their body, as shown in FIG. 21.

Pilot Studies

Pilot studies of the Tracheostoma Sealing Device were carried out at the Department of Clinical Medicine at Aarhus University, Denmark.

The feasibility of a device for sealing a tracheostoma was investigated in pilot studies in a porcine model of Danish Landrace Yorkshire of 60 kg. The study included 10 animals and was been approved by The Animal Experimentation Council under the Danish Ministry of Food, Agriculture and Fisheries (Journal No. 2014-15-0201-00265).

The study systematically assessed the functionality of the device in a number of different ways:

Foreign body analysis: 2 devices were implanted subcutaneously without intra-tracheal placement Surgical tracheostomy with insertion of a hyperflexible silicone tracheostomy tube (Biovona Adult Hyperflex XL fixed flange tracheostomy tube, cuffless) to mature a tracheostoma.

Post decannulation insertion of the sealing discs using the insertion sheath having the disc mounted in the barrel and deployed by pushing the plunger.

Having the external cover placed in the subcutis of the pigs to avoid dislocation of the device.

A percutaneous dilation tracheostomy technique was used to minimize the surgical intervention using: C-PTS-100-HC Ciaglia Percoutaneous Tracheostomy Introducer Set EZ Pass.

Insertion of the sealing disc through a tracheostomy tube (Tracheostomy Tube Blue Line Ultra cuffless internal diameter 8.0).

Having the external cover fixated on the outside of the animal neck using nylon sutures and a circular bandage to keep the device in place.

Using computed tomography to visualize the position of the devices before and after extraction.

After euthanasia, tissue was excised for histologic analysis of representative samples of the areas around the stoma (the stoma channel and trachea)

Postoperative Care

The animals were kept under observation on a daily basis for any sign of adverse effects and bandages were changed as required. The study period lasted 3 weeks. Injections of analgesics were administered 3 times a day for 3 days. Feeding troughs were replaced by flat bowls placed on the floor.

Animal No. 1. Foreign Body Test. (No extraction of a disc)

Animal No. 2. The disc was cut out with a block of tissue to "eyeball" the intact sealing disc on the tracheal wall. It was intact and experimentally I extracted it through the healed tracheostoma by pulling the tension thread. It had been a question if the tension thread could bring out the whole disc, and it did without unravelling the sealing disc, with no breakage. This was meant to simulate "patient panic test". The test showed that the device should be safe in the situation of manipulation of the external device (for example, if a confused patient attempted to remove the device).

Animal No. 3. Control experiment, only treated with a tracheostomy tube.

Animal No. 4. Device treatment 6 days. The sealing member was broken and removed from the animal.

Animal No. 5. Euthanathised during tube treatment due to tube displacement. No device treatment.

Animal No. 6. Device treatment for 14 days. The sealing member was broken and removed from the animal.

Animal No. 7. The sealing member was broken and removed from the animal. There was complete unravel of the spiral in one movement.

Macroscopic evaluation of the tissue involved at the insertion site (tracheal wall and channel between skin level and trachea) was good, with no signs of infection and no signs of necrosis. The tracheostomal channel healed and unimpaired.

Results:

Having the external cover fixated outside the neck has shown up to be appropriate as long as the need of bandage changes were considered on a daily basis. In the study, 4 animals had the sealing device inserted into the trachea (2 animals wore the device for 6 days, 2 animals wore the device for 2 weeks). All 4 animals showed unimpaired effortless respiration during treatment. The placement of the devices was visualized by a CT scan before removal of the device. All 4 animals had the sealing disc in the intended position at the front wall of the trachea and the CT imaging also excluded tracheal dilation and tracheal stenosis.

Histologic analysis was performed by the Department of Forensic Medicine at Aarhus University, Denmark. Representative samples of the profound tracheostoma and the tracheal wall involved did not show signs of infection and did not show signs of necrosis. The tissue analysis in general showed inflammation corresponding to a wound healing process.

Figure 22:
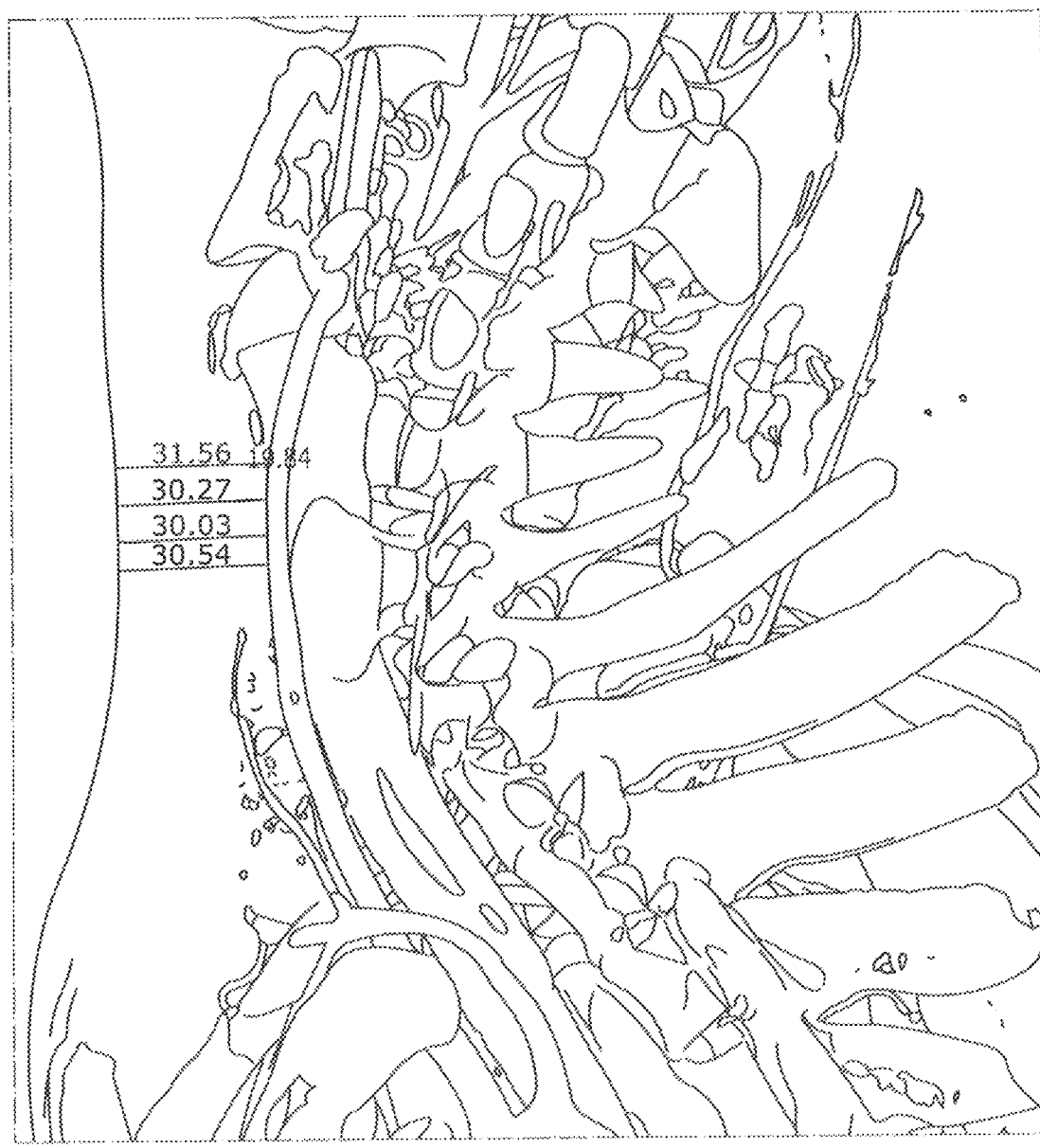
FIG. 22 is a CT scan of the anatomy of the pretracheal tissue of a pig prior to surgery.
Figure 23:
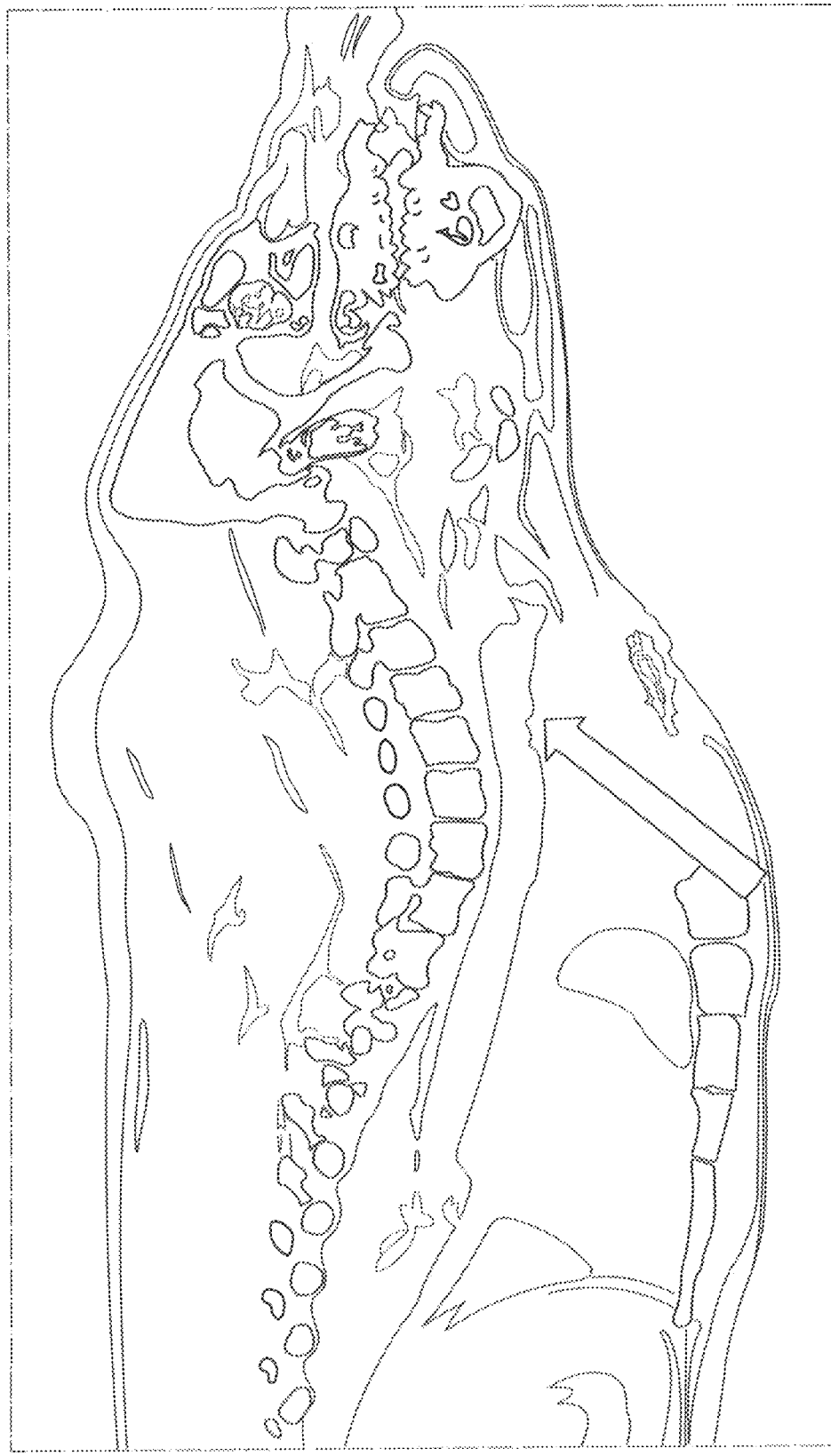
FIG. 23 is a CT scan, sagittal plane, showing a seal in place in the trachea of a pig.

A computed tomography (CT) scan was conducted to investigate the anatomy of the pretracheal tissue of a pig prior to surgery. The result is shown in FIG. 22, which contains measurements of tissue depth from skin level to the carotid artery. This information was useful in planning and conducting the surgery, to prevent damage to the blood supply FIG. 23 shows the results of a CT scan, sagittal plane, showing the seal in situ at the front wall of the trachea six days after the insertion of a seal of the invention into a pig. The animal was anaesthetised and spontaneously breathing during the procedure. The tracheostomal lumen is not visible (it has healed).

Figure 24:
FIG. 24 shows a CT scan, transverse plane, of a seal in place in a pig.
Figure 25:
FIG. 25 is a CT scan showing a seal and cover in place in a pig.

FIG. 24 shows a CT scan, transverse plane, of the seal member inserted in a pig. The seal is seen as a white U-shaped line at the ventral wall of the trachea. FIG. 25 is the result of a CT scan with 3D visualisation of the seal in intended position at the front of the trachea and the external cover implant in the pretracheal soft tissue.

FIG. 25 shows a CT scan with 3D visualisation of the seal in the intended position at the front of the trachea and the external cover implanted in the pretracheal soft tissue of a pig.

In addition to the CT scan, endoscopic photography was used to view the position of the seal when inserted in the animal trials. The investigations confirmed that the seal was correctly in place sealing the stoma, sticking close the tracheal wall and maintaining patent airway.

Preferences and options for a given aspect, feature or parameter of the invention should, unless the context indicates otherwise, be regarded as having been disclosed in combination with any and all preferences and options for all other aspects, features and parameters of the invention.

The listing or discussion of an apparently prior-published document in this specification should not necessarily be taken as an acknowledgement that the document is part of the state of the art or is common general knowledge.

The invention claimed is:

1. A device for sealing a tracheostoma in a patient, comprising a seal member for insertion through the tracheostoma to a trachea, wherein the seal member comprises a disc having a predetermined line of weakness, wherein in a first configuration the seal member forms a seal by being pulled against the tracheostoma, and wherein in a second configuration the seal member is removed from the trachea through the tracheostoma by breaking along the line of weakness.

2. A device according to claim 1, wherein the seal member comprises a first thread attached to the disc, wherein the disc is broken along the predetermined line of weakness by pulling the thread.

3. A device according to claim 2, further comprising a second thread attached to the disc.

4. A device according to claim 3, wherein the second thread is attached to a central portion of the disc.

5. A device according to claim 3, wherein the first thread is attached to a peripheral portion of the disc, and the second thread is attached to a central portion of the disc.

6. A device according to claim 3, wherein the first thread and/or the second thread comprise polypropylene, polyester or polyamide.

7. A device as claimed in claim 3, further comprising an external cover, wherein the external cover comprises attachment means for the device.

8. A device according to claim 7, wherein the attachment means comprises attachment means is for the first thread and/or second thread.

9. A device according to claim 7, wherein the attachment means comprises is a spring.

10. A device according to claim 7, further comprising a tube for inserting the device through a patient's tracheostoma.

11. A method of constructing a device as defined in claim 3, comprising moulding a disc as defined in claim 3 of material with a predetermined line of weakness and attaching a thread to the disc.

12. A method according to claim 11, wherein the disc is formed by injection moulding or polymer casting.

13. A device according to claim 2, wherein the first thread is attached to a central portion of the disc.

14. A device according to claim 2, wherein the predetermined line of weakness is a spiral.

15. A device according to claim 2, wherein the disc is substantially circular.

16. A device according to claim 2, wherein the disc is about 20 mm to about 40 mm wide and about 0.5 mm to about 3 mm thick.

17. A device according to claim 2, wherein the disc comprises silicone, polyvinvyl chloride, nylon, polypropylene, polyurethane or PTFE.

18. A method of constructing a device as defined in claim 2, comprising providing a sheet of material, cutting a disc as defined in claim 2 from the sheet, forming a groove to define a line of weakness, and attaching a thread to the disc.

19. A device as claimed in claim 1, comprising radiopaque material.

20. A method of sealing a tracheostoma in a patient, comprising providing a device as defined in claim 1, inserting the sealing member through the tracheostoma into the patient's trachea, and pulling the sealing member to form a seal against the tracheostoma.

* * * * *